United States Patent [19]
Berg et al.

[11] Patent Number: 5,247,461
[45] Date of Patent: Sep. 21, 1993

[54] METHOD AND APPARATUS FOR COINCIDENCE CORRECTION IN ELECTROZONE PARTICLE SENSING

[75] Inventors: Robert H. Berg, Elmhurst, Ill.; George Bakalyar, Crawford, Colo.

[73] Assignee: Particle Data, Inc., Elmhurst, Ill.

[21] Appl. No.: 738,119

[22] Filed: Jul. 30, 1991

[51] Int. Cl.$^5$ .................. G01N 9/00; G06F 15/20
[52] U.S. Cl. ....................... 364/555; 364/554; 364/571.01; 364/571.05; 324/71.4; 324/464; 73/865.5
[58] Field of Search .............. 364/555, 554, 571.01, 364/571.05; 73/865.5; 324/452, 464, 71.4

[56] References Cited

U.S. PATENT DOCUMENTS

| | | | |
|---|---|---|---|
| 3,626,164 | 12/1971 | Pontigny et al. | 364/555 |
| 4,447,883 | 5/1984 | Farrell et al. | 364/555 |
| 4,488,248 | 12/1984 | Okada et al. | 364/555 |
| 4,510,438 | 4/1985 | Auer | 324/71.4 |
| 4,612,614 | 9/1986 | Deindoerfer et al. | 364/555 |

FOREIGN PATENT DOCUMENTS 2033119  5/1980  United Kingdom .............. 324/71.4

Primary Examiner—Jack B. Harvey
Assistant Examiner—Hal D. Wachsman
Attorney, Agent, or Firm—Hill, Steadman & Simpson

[57] ABSTRACT

A method of correcting first approximation data obtained from a conventional electrozone particle sensing apparatus includes steps for calculating factors for correcting for binary and tertiary coincidences, from the raw data and from physical characteristics of the sensing equipment, to yield an accurate measure of particle distribution within the sample.

6 Claims, 12 Drawing Sheets

FIG.1a 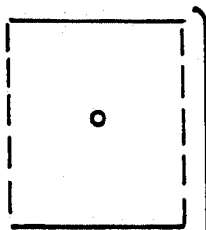 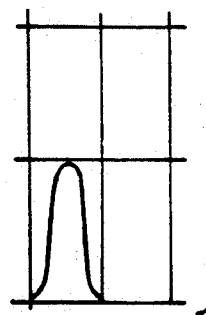
FIG.1b 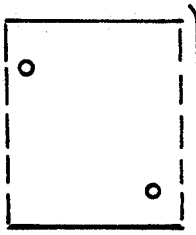 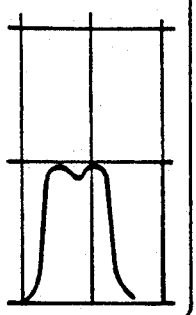
FIG.1c 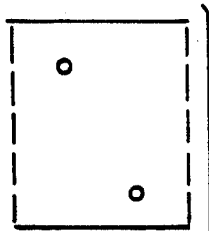 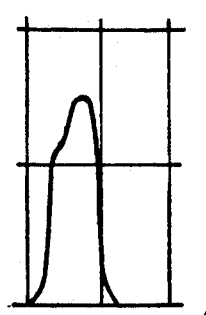
FIG.1d 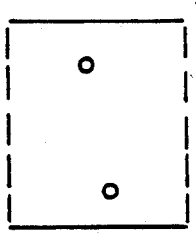 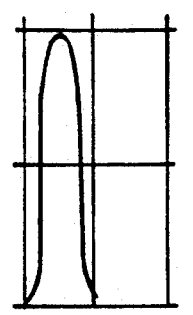

METHOD AND APPARATUS FOR COINCIDENCE CORRECTION IN ELECTROZONE PARTICLE SENSING

FIELD OF THE INVENTION

This invention relates to a method of obtaining an accurate representation of the size distribution of particles in a fluid sample, using a conventional particle detecting apparatus.

BACKGROUND OF THE INVENTION

Particles flowing serially and randomly through an electrical field constriction produce a series of electrical pulses, which may be detected by commercially available electrozone particle sensing equipment. Electrozone sensing responds to the displacement volume of each particle as the amplitude of its electrical pulse, thus providing the basis for electrozone particle size analysis (PSA) via a frequency histogram. Statistical adequacy (quantitative) is readily achieved.

In automated particle size analysis, the electrozone method has three intrinsic advantages in the elements of precision; true size sensing, low side effects and simplicity. These result in response purity and sensing reliability that make it naturally superior to the other major automated methods, sedimentation and various light beam interference methods including forward scatter, obscuration, diffraction and beam transit time.

All of these PSA methods use a fluid suspension of particles and all require the concentration of particles to be low enough to allow discrete particles mainly to generate the measurement signal, whether derived from a single particle or the massed effect of multiple particles of approximately equal size. With increased concentration, all PSA methods have increased inter-particle interferences, termed "sensing zone coincidence" in sensing zone methods, "concentration effect" in massed effect light scattering methods, "hindered settling" in sedimentation methods. As concentration is increased through the region of significant interference, the distribution histogram becomes increasingly distorted and eventually a state is reached where it is based on virtually no signals generated from discrete particles and is therefore usually useless.

The precision that is possible with the electrozone method provides the highest quality of measurement fidelity and hence a unique possibility for mathematical elimination of coincidence effects that produce unacceptable data distortion.

In the prior art, attempts have been made to correct for coincidence in single particle sensing when using an optical measuring technique, but in optical systems a correction is not practical due to multiple secondary responses of the light beam interference sensors, which seriously compromise the meaning of the pulse amplitudes which are realized. Secondly, the attempt to treat the optically generated pulses deals only with binary coincidence, and does not consider the significant effects of tertiary or higher levels of coincidence. Moreover, previous attempts to compensate for particle coincidences do not recognize the possible degrees of additivity of the component particle signals or the probability of pulses occurring during the dead time following recognized pulses, nor do they attempt to make the coincidence correction on a real time basis, i.e., within one minute.

The electrozone principle has three intrinsic advantages over the sedimentation or light beam interference methods which make it uniquely able to utilize rigorous mathematics for distributional coincidence correction.

In detail, the three aforesaid intrinsic advantages of the electrozone method are:

1. The truest measure of particle size, sensing the displacement volumes of individual particles in an electrical field, with the proportionality being true to a fraction of a percent from less than 0.5 to more than 1000 micrometers.

In light beam interference, particle size is sensed as a projected area "seen" by the light beam. On this basis, the size of a man would be described by his shadow's area without the sun's position being known, instead of his weight. In sedimentation, sensing is based on the surface area subject to fluid drag at the extant particle orientation. In both cases, errors can be enormous. Also, area sensing ($D^2$) has much lower resolution than volume sensing ($D^3$).

Further, none of these area responsive methods has a consistent response sensitivity throughout its size range. The response in light beam interference is increasingly poor as size drops below the five to seven micron region, and sedimentation rates may be exceptionally slow for smaller sizes and non-spherical particles by some orders of magnitude.

2. The least side effects in sensing: shape response amounts to a few percent of diameter at most, conductivity response is readily avoided, there are no significant effects from other physical properties of particles or suspension liquids.

Light beam interference methods are greatly affected by shape as well as refractive index, opacity and absorption. Sedimentation is also highly sensitive to particle shape, as well as particle density, optical properties (when using light beams), and to liquid (or gas) density, convection and viscosity (note falling ball or falling needle viscometers).

3. The simplest sensor structure, allowing highest stability and lowest costs. Electrozone employs merely a simple hole vs. a multi-instrument sensor for the said other major methods: beam source, optical train, photic receptor, plus (in sedimentation) a temperature/convection control system, plus (when accelerated) a centrifuge control system.

Electrozone calibration may be general (accurate to within a few percent) or of pin-point precision through easily used standard particles, narrowly distributed. Precise calibration allows accuracy within a few tenths of one percent (stating size as "volume equivalent spherical diameter").

Calibrations for sedimentation and light beam interference methods are done by theoretical response equations or by the use of specific materials having known distributions or by narrowly distributed standards. Data blurring, due to the compromises of side effects and multi-particle response as described above, is evidenced, e.g., by a marked spreading of the distributions for narrowly sized standards. Because of the compromises, these area sensing methods can only be calibrated for specific applications.

In the electrozone method for counting and sizing of individual particles there is inevitable coincidence in the sensing zone. The portion of the total particle population so involved is termed the "particles dedicated to coincidence" (PDC). Its distribution histogram shape is the same as that of the total population.

The total coincidence effect on the entire population is a net loss of particle count. The distributed coincidence effect is the gain and/or loss of count at every increment or channel of particle size. The algebraic sum of the distributed coincidence throughout the population equals the total coincidence.

In the literature, the total count loss is referred to as "primary coincidence", and the pseudo-distribution formed from distributed coincidence is referred to as "secondary coincidence". Pulse shapes formed by various degrees of particle proximity in coincidence have been described (FIG. 1).

SUMMARY OF THE INVENTION

Particle concentration, electrolyte conductivity, orifice size, and electric field gradient are selected to cause a sequence of measurable particle pulses each pulse defined by a rise from and return to an electrical level set above a steady state base line. Each pulse represents a passage of a single particle or the coincidence passage of two or more particles. Pulse amplitude for a single particle is proportional to its volume, enabling precise size analysis for suspensions that are dilute enough to ensure virtually no coincidence.

For multi-particle passages, the pulses are superimposed signals having amplitudes ranging from that for the largest particle to the sum of the amplitudes for the coincidence particles, it is illustrated in FIGS. 1A-1D. FIG. 1A illustrates a cross sectional view of an orifice at the time a single particle passes through it, with the resulting pulse which is produced. FIG. 1B illustrates a condition in which two particles, widely separated, are present in the orifice at the same time, with the modified pulse it results therefrom. FIG. 1D illustrates a condition in which the two particles pass through the orifice in nearly side-by-side condition, with the resulting pulse, and FIG. 1C shows the condition intermediate the conditions of FIGS. 1B and 1D.

Even with high speed pulse shape analysis multi-particle pulses cannot reliably be segregated from single particle pulses because of the multiple possible causes of irregular pulse shape. Therefore, all pulses must be assumed to be valid, resulting in distortions of count and size analysis data by the multi-particle pulses and missing single particle pulses.

Specifically, the primary effect is a loss of count for the particle population, due to the undetected particles in multi-particle pulses. The secondary effect, due to the spurious pulse amplitudes for coincidence passages and the missing single particle pulses, is distortion of the size distribution data, shifting it toward the larger diameter particles.

In electrozone sensing, particle properties other than size have negligible effects. Therefore, the removal of histogram distortion due to distributed coincidence will result in nearly perfect PSA. Given such distributed coincidence correction (DCC), the particle concentrations in the analysis samples may be increased twenty times or more, with correspondingly shorter time for distortion-free analysis and lower operator burden.

A mathematical treatment for DCC in a photic sensing zone has been described. In this approach, an approximate pseudo-distribution is generated from the observed distribution by integration. This approximation is subtracted from the observed distribution to obtain an approximate true distribution. The pseudo-distribution that is recalculated from this approximate true distribution is said to be negligibly different from the first calculation. If it were significantly different, the recalculated pseudo-distribution could be used instead. In any case, the true distribution so obtained is then scaled up to include the PDC as determined by Poisson statistics.

The present invention uses means for accelerated generation of a pseudo-function that is negligibly different from that generated by a lengthy integration process, but is much more rapidly obtained.

The observed PSA histogram, which is sometimes hereinafter referred to as a first approximation, has embedded within it both a true particle size distribution and a spurious distribution of coincidence-formed pulses. This invention allows clear separation of the spurious distribution and from this the generation of a complete, true distribution.

Three functional relationships are present:

(1) the probability of two or more particles, randomly grouped from the population, being coincident in the sensing zone, (2) the signal additivity for the various degrees of proximity of the particles co-present in the sensing zone, (3) the size distribution histogram, expressing the probability of presence of each size.

Enlarging on these:

(1) When particles are randomly scattered in space, the probability of coincidence in a given zone is based on Poisson statistics. Thus, for a given order of coincidence (binary, tertiary, etc.), one may determine the fraction of the total population that constitutes "particles dedicated to coincidence" (PDC).

(2) As to zonal proximity, note that in pulse detection the pulse ends are sensed when they cross a low "event threshold". In binary coincidence: minimum proximity occurs when two pulses are at the maximum separation where crossing of the event threshold does not occur between the pulses; maximum proximity occurs when the two pulses are exactly superimposed.

The proximity of two particles, A and B, then ranges from the minimum proximity where A precedes B, to the maximum proximity of exact superimposition, to the minimum proximity where B precedes A.

The additive signal caused by superposition of the pulses has five phases:

a) where the first pulse's ending is in the span between the second pulse's starting and its first maximum, which phase has NO additivity;

b) where the first pulse's maximum is in the span between its last position in a) and its first matching with the second pulse's maximum, which phase has PARTIAL additivity;

c) where the first pulse's maximum is in the span where it is matching the second pulse's maximum, which phase has FULL additivity;

d) mirroring of b), with PARTIAL additivity;

e) mirroring of c), with NO additivity.

(3) The distribution histogram of the PDC has the same shape as that of the total true population. Both are in effect expressions of the probability of presence of each size.

Distributed coincidence correction requires the satisfactory determination of the pseudo-distribution. Then, by subtracting it from the observed distribution, the true distribution results.

The PDC originates the pseudo-distribution which thus must be found by computing it from the PDC. The true distribution is unknown, so the observed distribution is used as the approximate shape of the PDC distribution. Given the volume of the sensing zone and the number of observed particle-pulses in a known volume of sample suspension, the total PDC count quantity is calculated from Poisson statistics.

Thus knowing the quantity and shape of the PDC distribution and the five phases of (2) above, the pseudo-distribution is determined by computing and summing, for each channel of the PDC distribution, the probabilities of all of the possible combinations of particles forming that channel.

The computation of count loss due to coincidence is based on the Poisson distribution of the particles in the suspension. However, the computation of the distribution distortion is much more complex. It is a principal object of the present invention to correct for distortion in the particle size distribution.

The present invention contemplates the actual distribution of the various sizes of particles in a major population, and the effects of possible particle combinations in binary and tertiary coincidences. A binary coincidence is one in which two particles pass through the orifice at the same time, and a tertiary coincidence is one in which three particles are present in the orifice at the same time. The probability of having four or more particles present in the orifice at the same time is quite low under practical measuring conditions, so that the conditions of coincidence of four or more particles may be neglected without loss of precision.

The present invention also considers the probability of all possible degrees of additivity of the component particle signals in the coincidences. The present invention also considers the probability of missing pulses, both single and multiple particle pulses, which may otherwise occur during the dead time following each pulse, devoted to recovery of signal processing electronics.

The rigorous treatment of the coincidence correction involves considerable computation as will discussed hereinafter. However, any system which requires long intervals of calculating time represents a serious handicap in the utility of the correction method. Particularly, in the circumstance of relatively rapidly changing conditions in the suspension, it is desirable to obtain a precise particle count and size distribution within a short period of time, in less than one minute, in order to provide a real time analysis for timely presentation of results. For that reason, the present invention enables the correction to be accomplished within less than one minute, using an available computer with modest speed and capacity.

The validity and effectiveness of the present invention has been demonstrated by comparing corrected data taken at a high level of coincidence, with data for a corresponding suspension taken at a very low coincidence.

The present invention accomplishes several benefits. First, data acquisition times at 20-30 percent coincidence are lower by 95-98 percent than those at under one percent coincidence, and since concentrations need not be carefully watched, sample preparation is easier. Reduced operation costs and speedier analysis results are significant advantages.

Secondly, acquiring adequate data in one to four seconds allows measurement of materials that, in such a short time after immersion in electrolyte, may significantly change (dissolve, fragment, agglomerate, etc.). Further, to study such changes, data sets may be taken and stored in rapid succession automatically, for later coincidence correction and analysis of changes.

Thirdly, the 95-98 percent time reduction for data acquisition means an equal reduction of background noise in the data set (see FIGS. 2 and 3). Such noise is proportional to sampling time and therefore electrolyte volume (fine debris).

Finally, removal of coincidence distortion greatly reduces the chances of questionable measurement. Undistorted distribution data coupled with standardized size scales allow precise comparisons between laboratories and product lots and exact matching for extrapolation and multi-range blending.

IN THE DRAWINGS

Reference will be made to the accompanying drawings in which:

FIG. 1, consisting of FIGS. 1a to 1d, illustrates a variety of conditions of multiple particles within the sensing zone;

Figure 3:
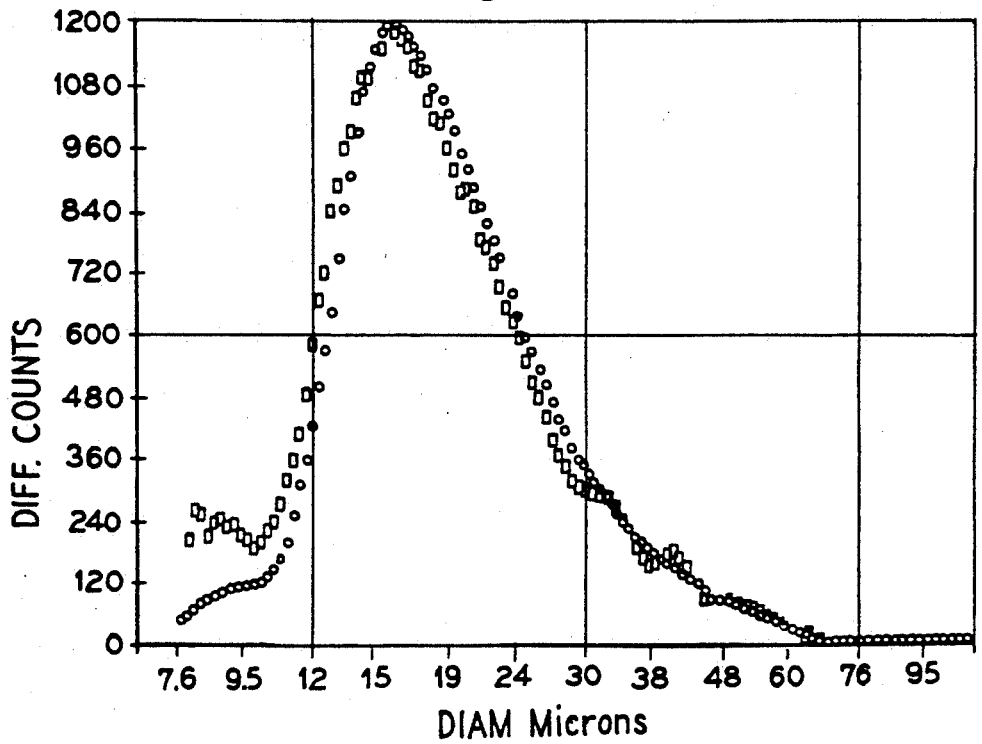
FIG. 3 illustrate two histogram plots indicating raw (first approximation) data and the same data which have been corrected in accordance with the present invention.

Referring now to FIG. 3, raw and corrected data taken from a sample having a relatively large number of coincidences, on the order of 20%, are illustrated in two curves, each of which is a histogram plotting particle diameter along the x-axis relative to the number of counts of particles of each size category along the y-axis. The curve 10 is the uncorrected curve, and the curve 12 is the curve which has been corrected in accordance with the present invention, which represents the true particle distribution. As illustrated in FIG. 3, the curve 10 is skewed rightwardly, toward large particles, because the coincidence of multiple particles within the sensing zone gives an indication of a larger particle than any one of the individual particles which are coincident. In addition, the total number of counts, which is the integral of the curve, is smaller for the uncorrected data, since those particles which are included in the coincidences are not counted, which occur during the coincidence period.

Figure 2:
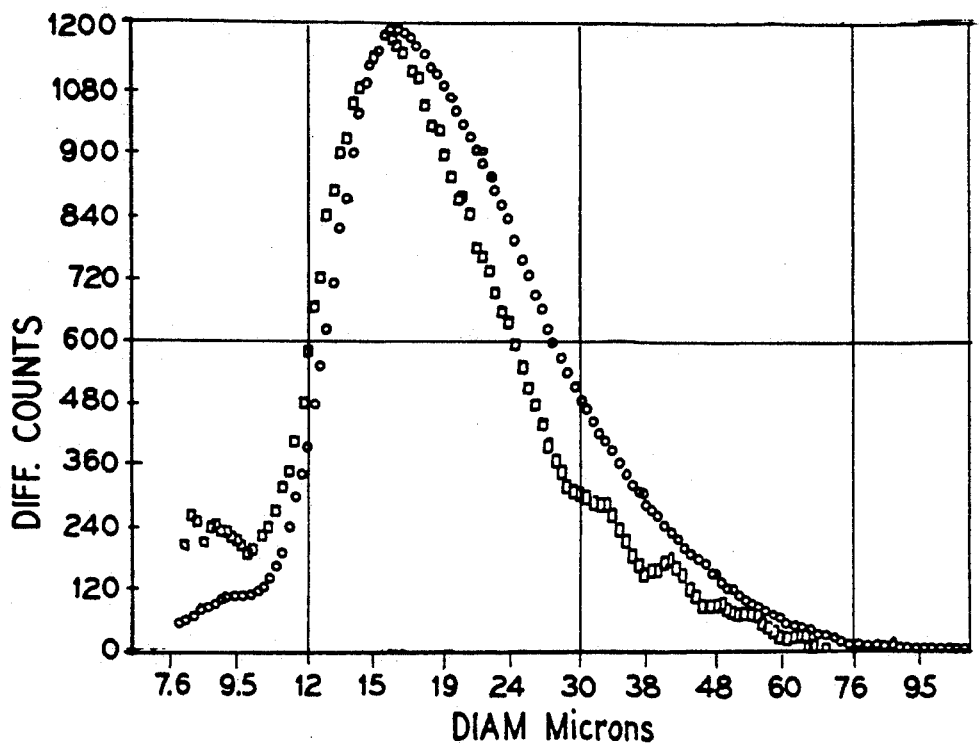
FIG. 2 illustrates two histogram plots, comparing data from a sample with relatively few coincidences, with data from a sample of the same material with a large number of coincidences, which data have been corrected in accordance with the present invention.

FIG. 2 illustrates the precision of the correction effected by the present invention. Curve 14 is the data taken from a relatively dilute sample, in which very few coincidences occur, on the order of 0.5%. The curve 16 is corrected data taken from the sample of the same particle distribution, in which a relatively large number of coincidences occur, on the order of 20%. As shown in FIG. 2, the present invention effects a very exact correction of the data, which corresponds closely to data taken from a sample with very few coincidences. Further, the noise at the small end of the high concentration sample is much less, as aforesaid.

An overview of the correction is expressed by Equation 1:

$$NCC[n] = \frac{(NTM[n] - NP2[n] - NP3[n])}{(1 - FC)} \quad (1)$$

Where:
$0 \leq n \leq C$
n is the channel number being corrected
C is the total number of channels, e.g. 128
NCC[n] is the corrected size histogram array
NTM[n] is the measured size histogram array
NP2[n] is the binary pseudo-spectrum array
NP3[n] is the tertiary pseudo-spectrum array
FC is the fraction of particles in coincidence in the measured volume, expanded to include deadtime.

The form of the binary array results from the detailed summing of all coincident size pairings (as extracted from elements of the PDC array, together with their associated probabilities) and the probabilistic effect of composite signal detection as they contribute count to a particular channel [n]. The tertiary array is produced by a recursion-like process, applied to the already computed binary array, which produces tertiary coincidence.

The algorithms for binary and tertiary coincidence operate on any form of PDC array. These pseudo-spectra are generated by the following computations for each channel [n] as counts added or subtracted as a consequence of binary or tertiary coincidence, in which two or three particles form but a single counted pulse.

The binary array is expressed by Equation 2:

$$NP2(X2[n]) = P1 * \left[ P2[n] + \frac{\ln 4}{Ca}(1 - f) * P3[n] \right] \quad (2)$$

Where:
NP2=the number of counts to be added or subtracted for channel [n]
X2[n]=NTM2[n]=the known measured PDC array,
P1=1/NT2
NT2=the estimated number of singlets in the doublet PDC array.

$$P2[n] = f * X2[n] \left( \sum_{j=0}^{n} \left( X2[j] - \frac{X2[n]}{2} \right) \right)$$

$$P3[n] = \sum_{a=0}^{Ca-1} \sum_{\delta=0}^{Ca-a-1} (X2[n - Ca + a + \delta] * CC)$$

$$CC = (2^{\frac{g(\delta)-a}{Ca}}) \sum_{i=0}^{A(\delta)} (2^{\frac{-i}{Ca}} X2[n - Ca + a - g(\delta) + i])$$

$$g(\delta) = \text{closest integer} \left( \frac{C/\alpha}{\ln 2} |\ln(2 - 2^{\frac{\delta}{C/\alpha}})| \right)$$

C=total number of channels, e.g. 128
$\alpha \geq 1$=span coefficient (not necessarily an integer), for example $\alpha = \log_2(C) = \ln[M] - (\ln[z0]/\ln 2)$
z0=minimum size at channel 0
M=maximum size=$z0 * 2^\alpha$ at channel C and the ln[size] at channel X is:

$$[z0 * 2^{\frac{X}{(C/\alpha)}}]$$

Ca=Floor C/$\alpha$=largest integer smaller than C/$\alpha$
$\delta$ and a=convolution variables
$\overline{A}(\delta) = g(\delta) - g(\delta - 1)$
i=summing index
f=a signal detection parameter, $0 \leq f \leq 1$
The tertiary array is expressed by Equation 3.

$$NP3(X3[n]) = P1 * \left[ P2[n] + \frac{\ln 2}{Ca}(1 - ff) * P3[n] \right] \quad (3)$$

Wherein:
Many terms are as defined above, but note that for this array, P1, P2[n], P3[n], CC and f definitions are modified.
NP3=the number of counts to be added or subtracted for channel [n]
X3[n]=NTM3[n]=m/3 X2[n]
m=NT * Vs/VT
NT=total number of particles in expanded volume
Vs=measured volume, without deadtime volume
VT=total (expanded) volume, including deadtime
X2[n]=NTM2[n]=the known measured PDC array
P1=2/NT3
NT3=the estimated number of singlet particles in the tertiary PDC array $$P2[n] = ff * X3[n] \left( \sum_{j=0}^{n} NP23[j] - \frac{NP23[n]}{2} \right)$$

$$NP23[n] = NP2[X2[n]] * \frac{NT3}{NT2} = \frac{m}{3} NP2[X2[n]]$$

$$P3[n] = \sum_{a=0}^{Ca-1} \sum_{\delta=0}^{Ca-a-1} (NP23[n - Ca + a + \delta] * CC)$$

$$CC = (2^{\frac{g(\delta)-a}{Ca}}) \sum_{i=0}^{A(\delta)} (2^{\frac{-i}{Ca}} X3[n - Ca + a - g(\delta) + i])$$

Terms $g(\delta)$ through ff are as defined for Equation 2.

Figure 4:
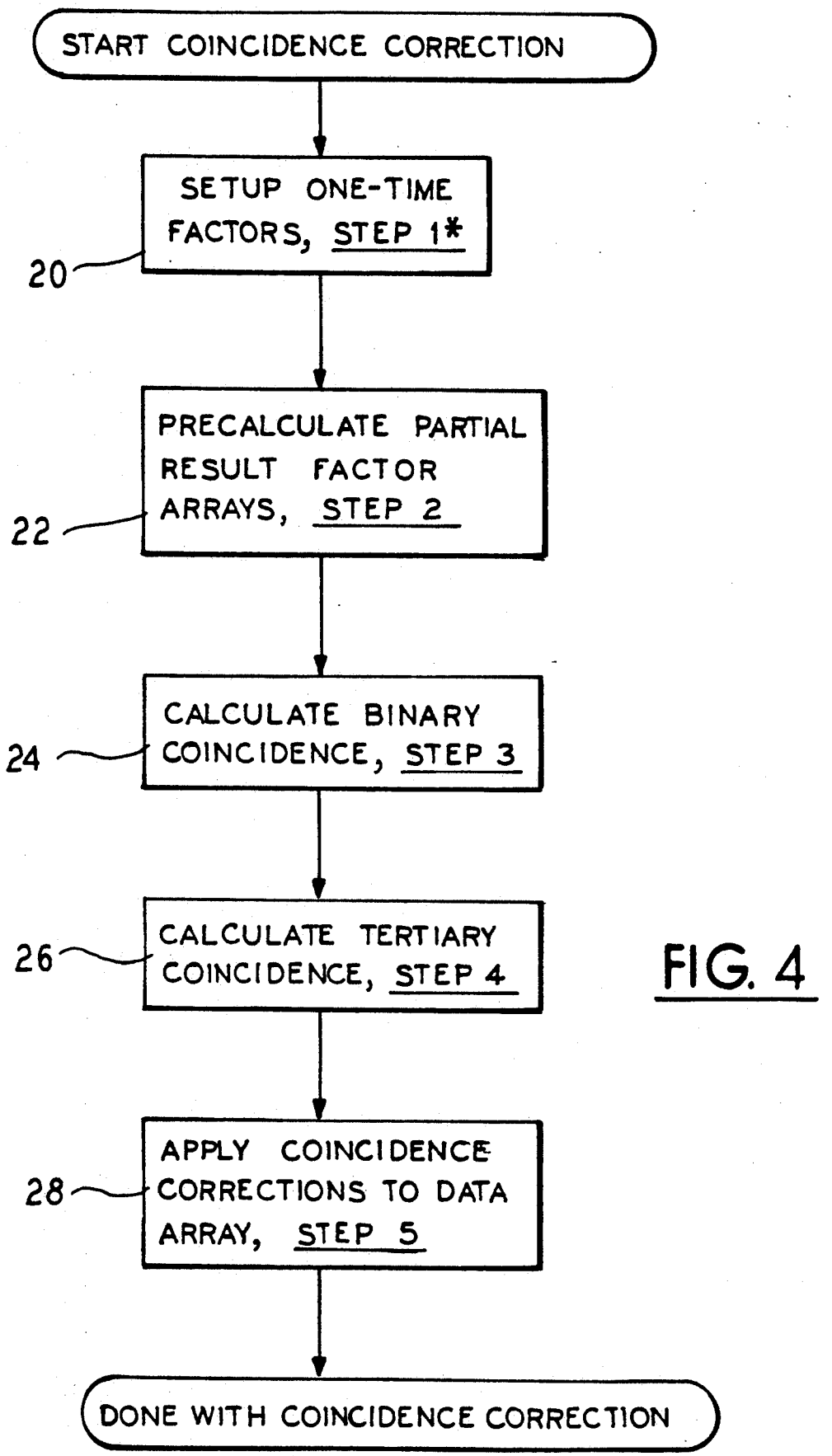
FIG. 4 is a flow chart illustrating the method of the present invention.

FIG. 4 illustrates the steps performed in the process of the present invention. It is convenient to perform the process by programming a general purpose digital computer to perform the steps in sequence. When a readily available computer is used for this purpose, the entire process takes less than one minute, so that the present invention can effectively be used in real time monitoring situations.

Alternatively, instead of using a programmed general purpose digital computer, it is possible to perform the method of FIG. 4 by means of apparatus incorporating dedicated hardware for the performance of each step, such as a special purpose computer. For this reason, subsequent discussion of the flowcharts will refer to the individual components of the flowcharts as "units", to emphasize that the units may be either steps performed in the execution of the program of the computer, or may be steps performed as the function of apparatus specifically dedicated to the respective components, in the nature of a special purpose computer.

When the process of FIG. 4 is performed, in step 1, constants and temporary variables used throughout the remainder of the process are calculated and stored. These factors are either optional constants or fixed constants. Optional constants include the number of channels into which the data is distributed, viz., the number of adjacent particle size bands in the histogram. Fixed constants include sensing volume, and the like, which are closely linked to the characteristics of the equipment which is not readily modifiable. The optional constants may be selected by an operator. Thus, the number of channels may be varied in order to provide a coarse or fine resolution in a histogram. In addition to the initial constants, arrays are typically defined and memory is allocated so that intermediate calculated values can be stored in array or matrix form. This occurs in unit 20, which performs step 1.

The constants and other factors calculated from them which are used in the calculation of the coincidence corrections are listed in Table 1.

TABLE 1

Initial Constants

| | |
|---|---|
| C | number of channels of data in the distribution. |
| Vs | Sensing volume, the amount of fluid that is present in the sensor zone. |
| VT | total volume of fluid run through the sensor. |
| tm | measuring time. |
| td | dead time of the sensor electronics |
| f and ff | signal detection parameters |
| Array [N] | measured size histogram as produced by instrument, at end of procedure, updated to show the true corrected count |

Calculated Intermediate Values $NTM = \sum_{i=1}^{N} CTM[i]$ = total measured count $D = NTM * Vs/VT * (1+td/tm)$
a constant containing all the measured parameters; also:

$D = mc/e^{mc-1} * \sum_{N=1}^{10} mc/N * N!$

Thus it follows,
mc is the solution of this equation and is the expected number of particles in the expanded sensing volume at any one instant taking into account the dead time. Expanded sensing volume is greater than the actual sensing volume because fluid is flowing during the dead time and not measured, therefore a greater volume of fluid is involved (lookup table interpolation). Cutting off the summation at N=10 saves time and effects the answer to within less than 0.01%.

$m = mc/(1+td/tm)$
expected number of particles in the measured sensing volume at any one instant $NT = (mc * VT/Vs) * (1+td/tm)$
estimated total true count $NTD = NT/(1+td/tm)$
estimated number of particles contained in volume of fluid sensed in the time period Tm $FC2 = e^{-m} * m^2/(2 * (1-e^{-m}))$
fraction of particles lost due to binary coincidence (a Poisson statistic)

$FC3 = FC2 * (m/3)$
fraction of particles lost to tertiary coincidence (a Poisson statistic)

$NT2 = NTD * FC2$
estimated number of particles participating in binary coincidence $NT3 = NTD * FC3$
estimated number of particles participating in tertiary coincidence $NCC2[i] = NT2/(NTM * NTM[i])$
size distribution array of binary coincidence particles, $1 \leq i \leq N$ $NCC3[i] = NT3/(NTM * NTM[i])$
size distribution array of tertiary coincidence particles, $1 \leq i \leq N$ $a = \log_2 C$
log of number of channels, which may be selected independently of C $Ca = Floor(C/a)$ = largest integer smaller than $C/a$
$K1 = (\ln 4/Ca) * (1-f)$ = common sub-expression
$K2 = (\ln 2/Ca) * (1-ff)$ = common sub-expression
$FC = 1 - (D/mc)$
the fraction of the total number of particles dedicated to coincidences, including deadtime The binary and tertiary coincidences are calculated in three parts. Part 1 is the same for each value, i.e, each particle size. Parts 2 and 3 are individual to each size:

$$Part\ 1 = 1/NT2$$

$$Part\ 2[n] = f * NCC2[n] * \sum_{j=0}^{n} MCC2[i] - NCC2[n]/2$$

$$Part\ 3[n] = \sum_{a=0}^{Ca-a-1} \sum_{\delta=0}^{Ca-a-1} [NCC2[n - Ca + a = \delta] * CC(a,\delta)]$$

The binary and tertiary correction are each calculated, for each value, as:

$$NP2[n] = Part\ 1 * (K1 * Part\ 2[n] + K2 * Part\ 3[n])$$

Then control passes to unit 22, which precalculates partial result factors, and stores the same in arrays. The arrays typically contain one element or storage location for each of the channels participating in the calculation of the partial results, so that intermediate results can be stored easily. Then control passes to unit 24, which calculates binary coincidence correction factors, meaning the amount by which the number of particles sensed for each particle size classification must be reduced (for large sizes), and increased (for small sizes) to account for coincidence of exactly two particles within the sensing zone. Then control passes to unit 26, which makes the corresponding adjustments to correct for the presence of three particles in the sensing zone at one time. Then control passes to unit 28, which applies the coincidence corrections calculated in steps 3 and 4 to the data array, so that the data array describes the correct particle size distribution of the sample. The corrected data may be displayed in the form of a histogram, either with a video monitor connected to the computer, or with a printout in the form of a histogram produced by a printer or plotter or the like.

Figure 5:
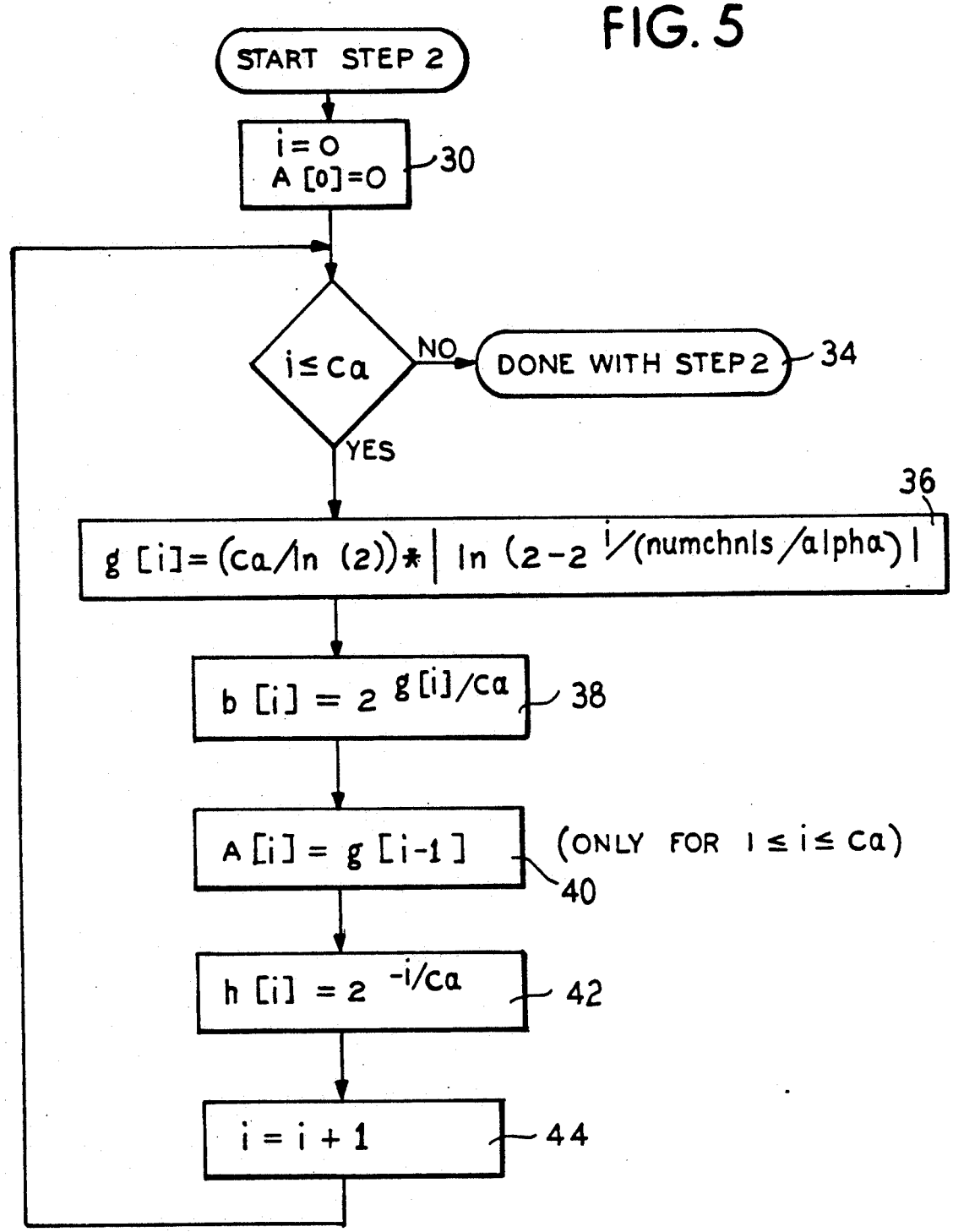
FIG. 5 is a flowchart of steps performed during step 2 of the process of FIG. 4.

Referring now to FIG. 5, the components of the unit 22 are illustrated. Unit 30 first receives control, which sets initial values to zero. The parameter i is an index, and the initial (zero) component of array A is set to zero. Then unit control passes to unit 32, which determines whether the index i is less than the value Ca. If not, control passes via path 34 to unit 46 of FIG. 6, described hereinafter. Otherwise, control passes to unit 36, which calculates and stores a result in element i of array g. Then control passes to unit 38, where another calculation is performed with the result stored in element i of array b. Then the contents of array g are read out and stored in array A, with the index of array A being one less than the source of the data in array g. Then control passes to unit 42, which performs the calculation and stores the results in element i of array h. Finally, unit 44, increments index i, and returns control to the unit 32. When control passes to FIG. 6, from unit 32, the loop of units 32-44 has been repeated a number of times, equal to the value Ca. The value Ca is a value which is calculated in step 1, and represents the range over which the first approximation data are adjusted, for each channel.

Figure 6:
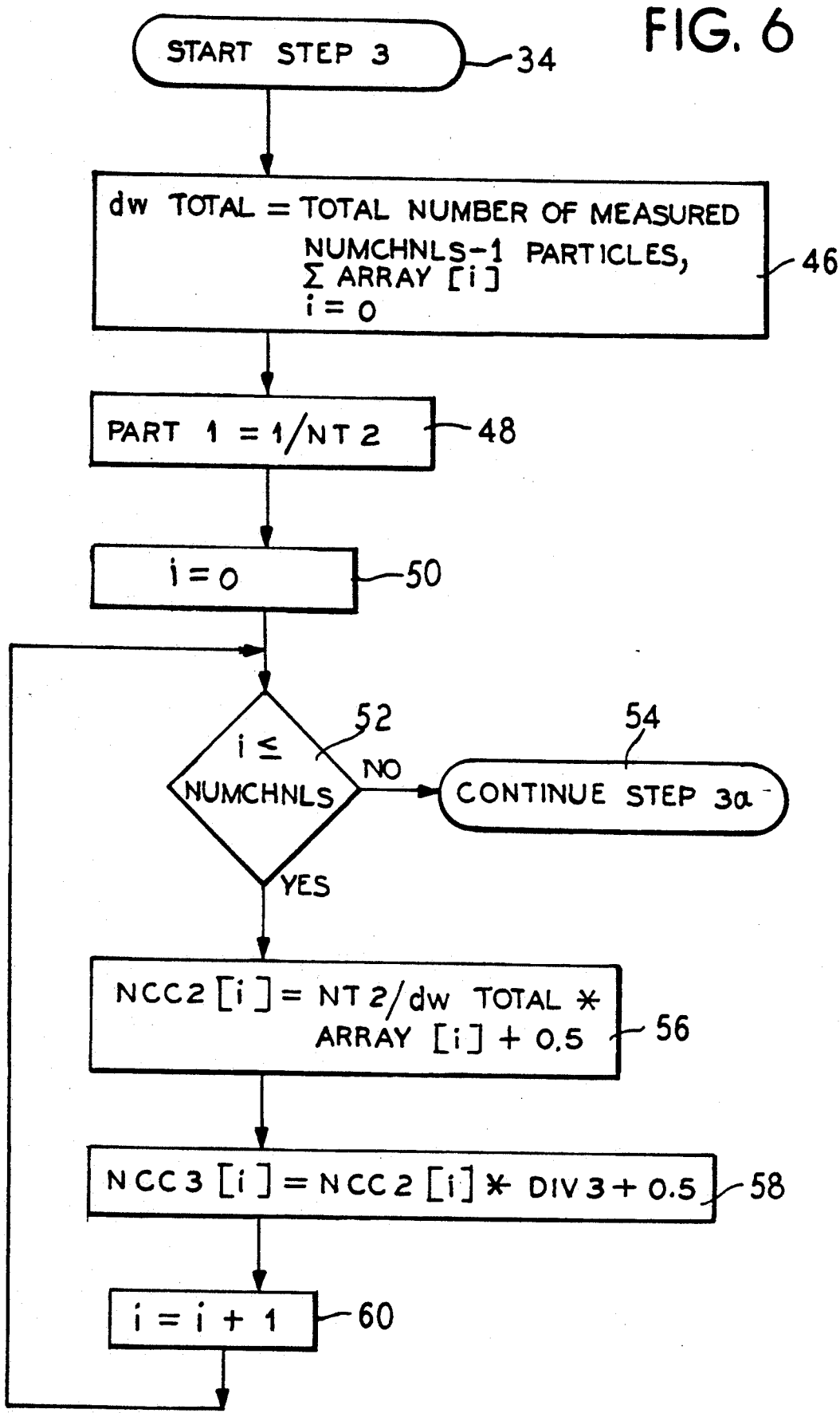
FIGS. 6 and 7 are first and second portions of the third step of the process of FIG. 4.

When FIG. 6 receives control from unit 32 of FIG. 5, control passes to unit 46, which calculates the parameter dwTotal. Then control passes to unit 48, which calculates "part 1", of the binary correction. Then control passes to unit 50, which sets the index i=0, then control passes to unit 52, which determines whether i has been increased to equal the total number of channels. If so, control passes over path 54 to FIG. 7. Otherwise, unit 56 receives control, and performs a calculation and stores the result in element i of array NCC2. Then unit 58 receives control, and performs a calculation, and stores the result in element i of array NCC3. Then unit 60 increments i and returns the control to unit 52. Thus, before control passes to FIG. 7, the loop of units 52-60 has been repeated for each of the total number of channels.

Figure 7:
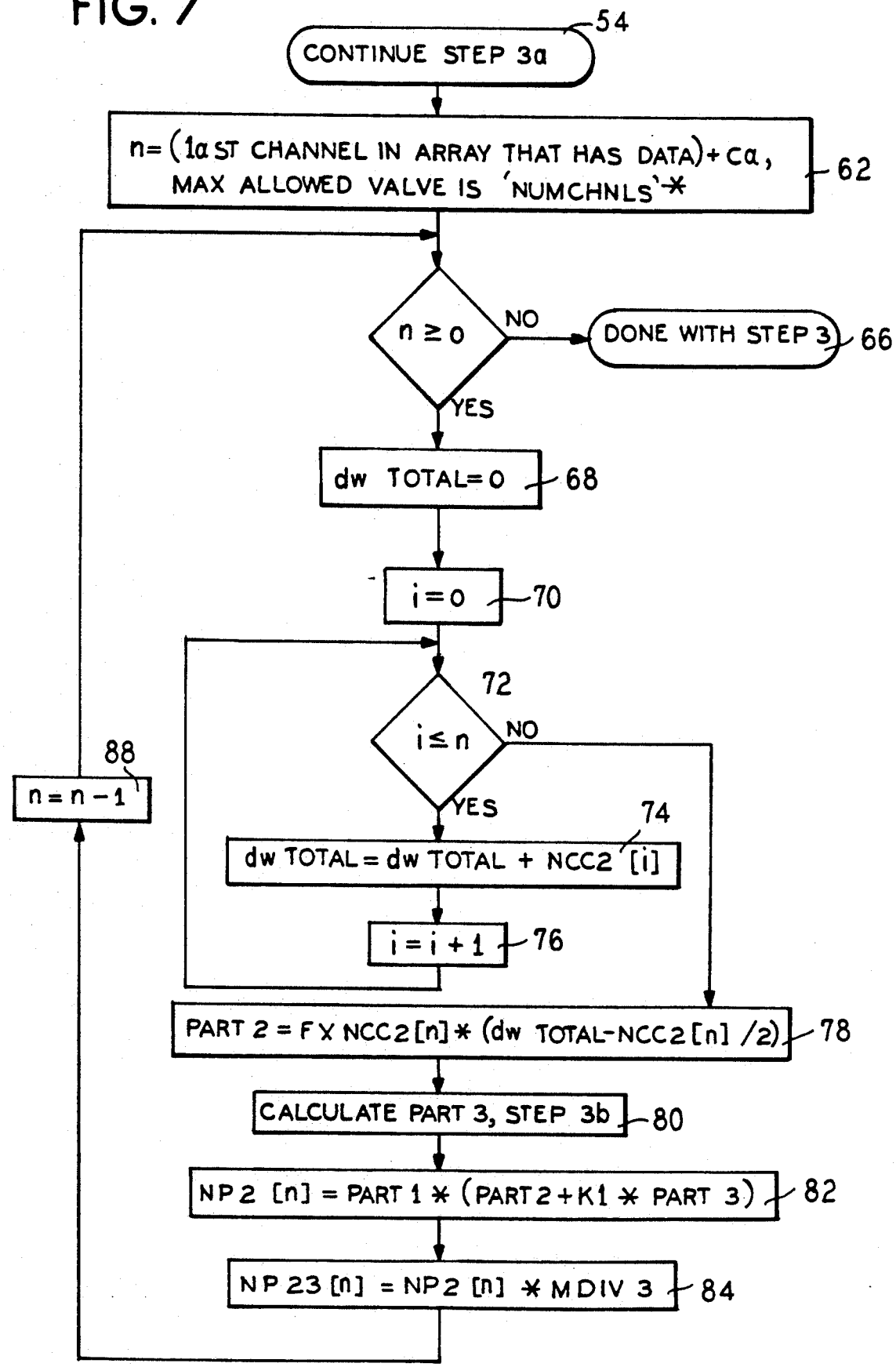

FIG. 7 receives control over path 54 and passes control to unit 62, which calculates a value for n, which is the last channel in the array that has data, plus the interval Ca, with the maximum allowed value being equal to the total number of channels. Then control passes to unit 64, which determines whether n is less than zero. If so, control passes over path 66 to step 4 of FIG. 4. Otherwise, units 68 and 70 set the parameters dwTotal=0 and i=0 and then unit 72 determines whether i has been increased to a value greater than n. If so, control passes to unit 78. Otherwise, unit 74 increases dwTotal for NCC2[i], then increments i in unit 76, and returns control to unit 72.

When i reaches a value greater than n, unit 78 calculates "part 2" of the binary correction, and then unit 80 calculates "part 3" of the binary correction; and then control passes to unit 82 which stores a calculated value derived from parts 1, 2 and 3 in element n of array NP2. Then control passes to unit 84, which makes a calculation and stores the result in element n of array NP23. The contents of the array NP23 are used for tertiary compensation, described hereinafter. Then control passes to unit 88, which decrements the value of n, and returns control to unit 64.

Figure 8:
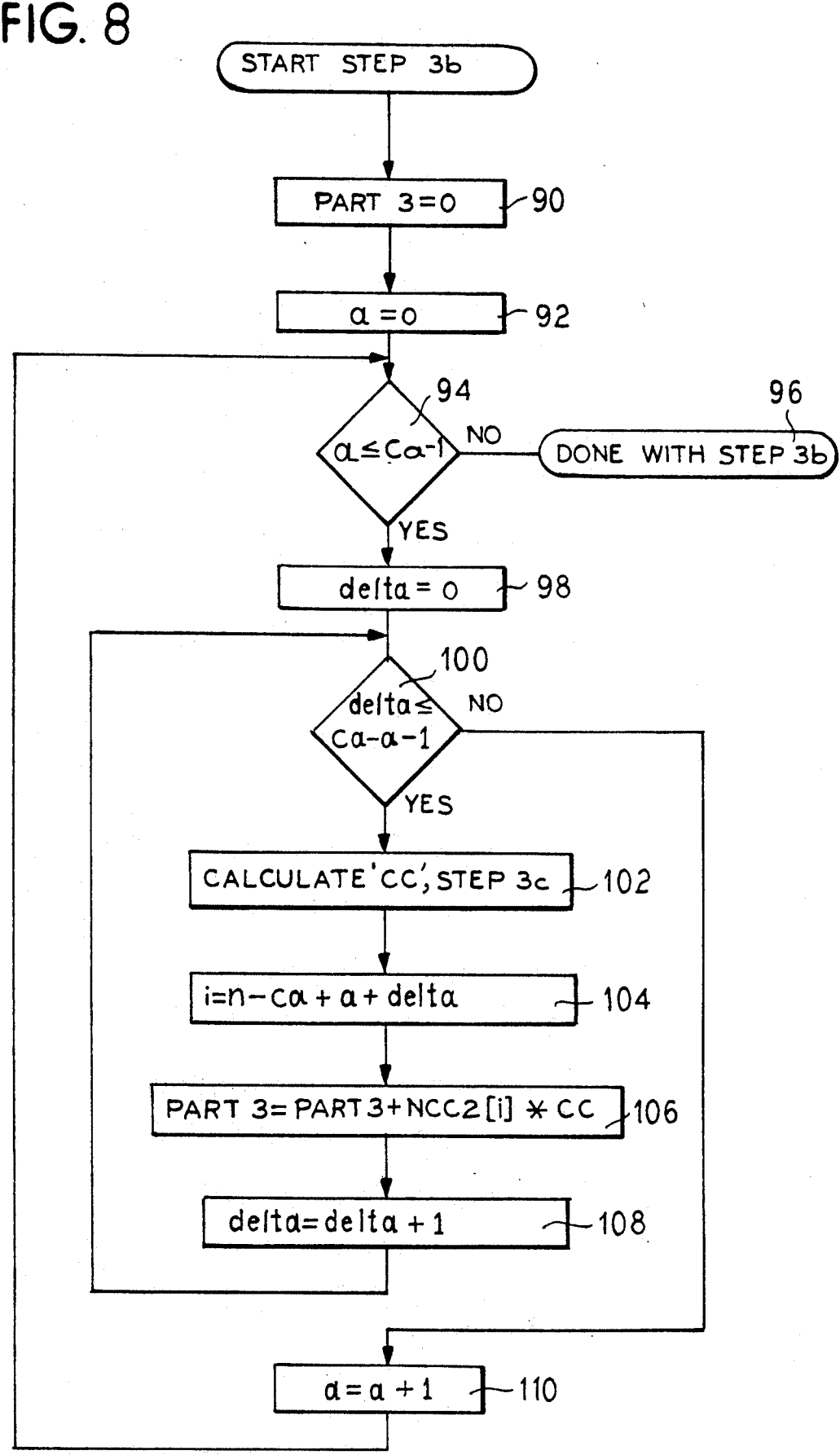
FIG. 8 is a flowchart of one of the steps of the process of FIG. 7.

FIG. 8 illustrates the units incorporated in the unit 80 of FIG. 7.

The unit 90 (FIG. 8) receives control from unit 78 (FIG. 7), and sets the initial value of "part 3" of the binary correction equal to zero. Then unit 92 sets an index parameter a equal to zero, and passes control to unit 94. The unit 94 determines whether a is greater than the value of Ca−1, and if so, passes control to an exit which in turn passes control back to unit 82 (FIG. 7). Otherwise, unit 98 receives control which sets a parameter "delta" equal to an initial value of zero. Then unit 100 determines whether the current value of delta is greater than Ca−a−1, and if so, passes control unit 110, which increments A and returns control to unit 94. Otherwise, control passes to unit 102, which calculates the value CC. Then unit 104 calculates an index i, which is used to access element i of the array NCC2, by unit 106, which receives control next. Then control passes to unit 108, which increments the value of delta and returns control to the unit 100. The loop incorporating units 100-108 is repeated until delta is increased to a value which exceeds Ca−a−1.

Figure 9:
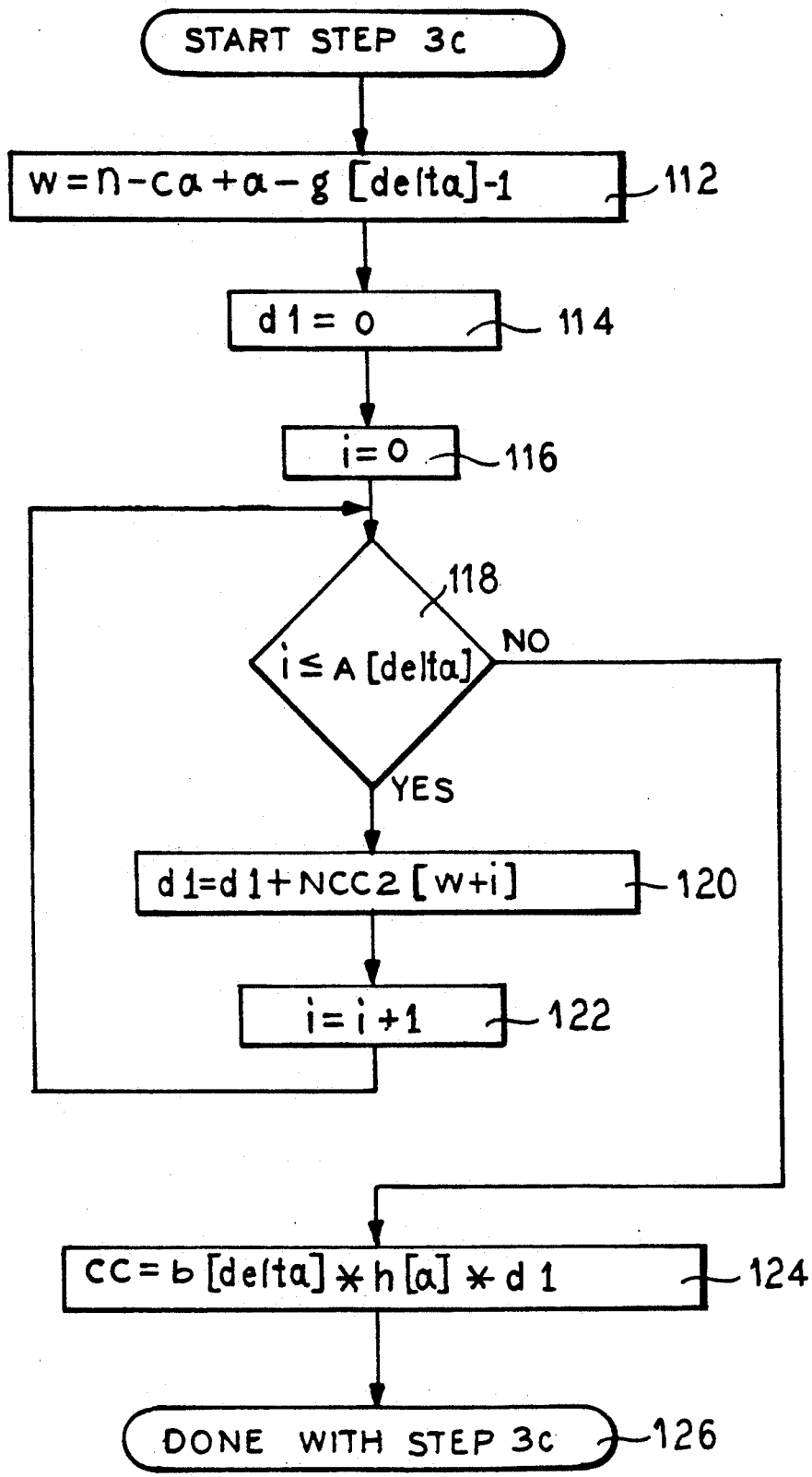
FIG. 9 is a flowchart of one of the steps of the process of FIG. 8.

The components of unit 102 are illustrated in FIG. 9.

FIG. 9 receives control from unit 100, for low values of delta, and control passes to unit 112, which computes a value for w (used by unit 120), after which indexes dl and i are set to zero by units 114 and 116. Then unit 118 determines whether i has been increased to a value which exceeds the delta component of array A, and if so, control passes to unit 124. Otherwise, control passes to unit 120, which calculates the value for dl by increasing the previous value of dl by the content of one of the elements of the array NCC2, namely, element w+1. Then the index i is incremented in unit 122, and control returns to unit 118. The loop incorporating units 118-122 is repeated until i exceeds the delta component of array A.

Unit 124 calculates the value for CC, and returns control to unit 104 (FIG. 8) over path 126.

Figure 10:
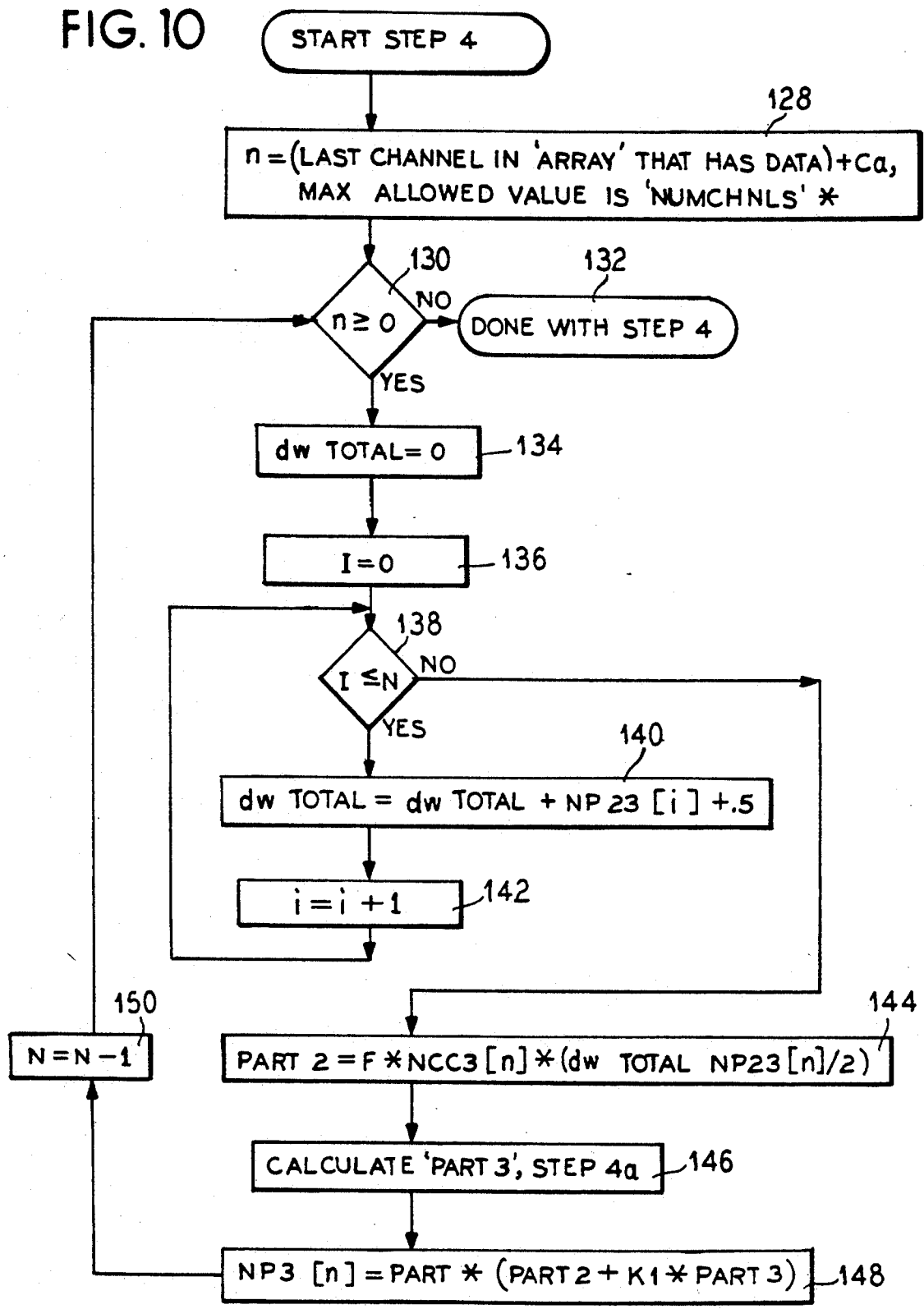
FIG. 10 is a flowchart of step 4 of the process of FIG. 4.

The components of unit 26 of FIG. 4, which calculates the tertiary correction factor, are illustrated in FIG. 10.

Unit 128 receives the control first, which recalculates the value of n, which is the same value of n calculated in unit 62 of FIG. 7. Then unit 130 receives control, which determines whether the value of n is less than zero, and if so, control passes over path 132 to unit 28 of FIG. 4. Otherwise, unit 134 sets the initial value of dwTotal equal to zero, and index i equal to zero, in units 134 and 136. Then units 138-142 perform a loop corresponding to the loop of units 72-76 of FIG. 7, after which units 144 and 146 calculate "part 2" and "part 3" for the tertiary correction, and unit 148 calculates the final tertiary correction and stores it in element n of array NP3. Then unit 150 decrements n and returns control to unit 130.

Figure 11:
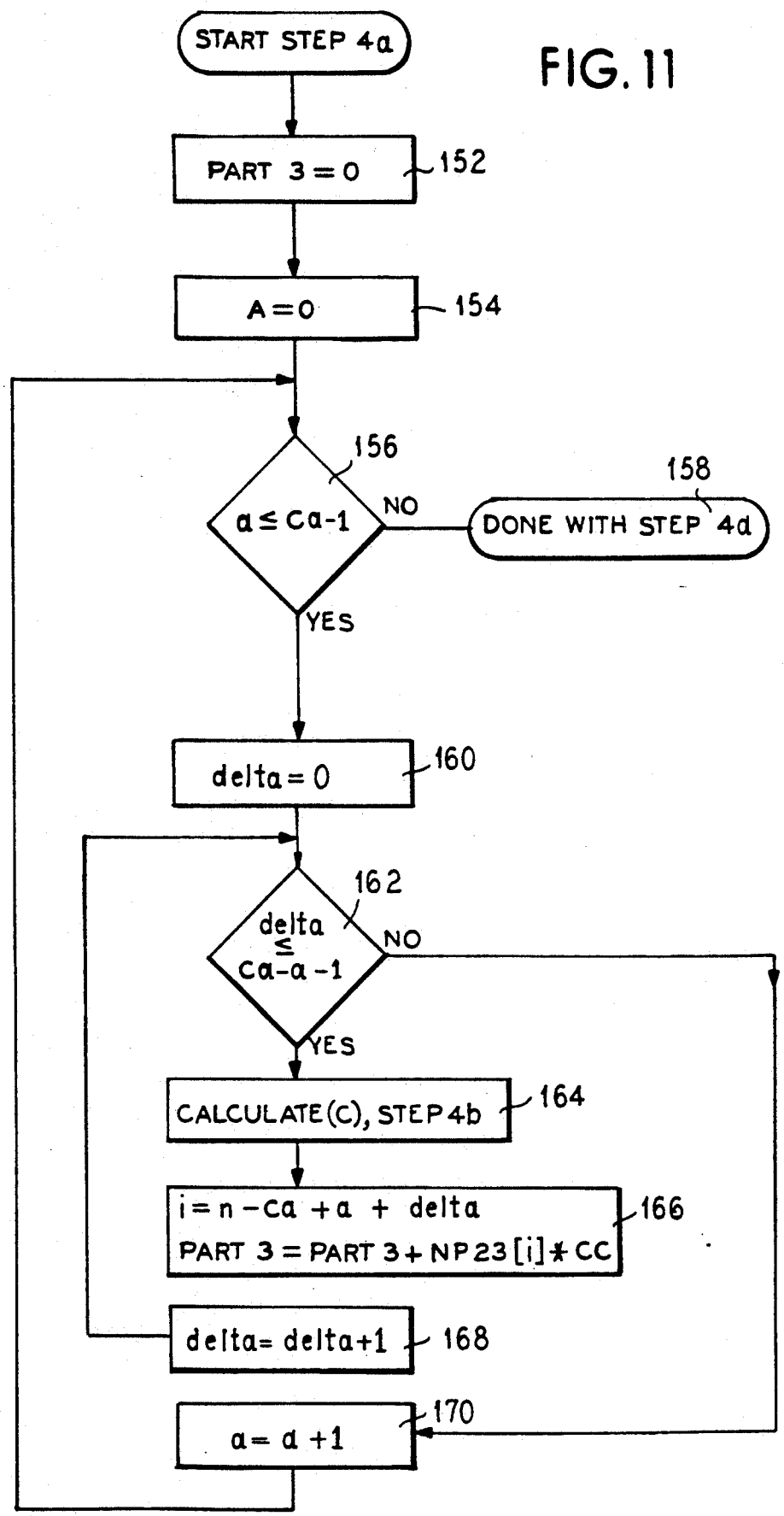
FIG. 11 is a flowchart of one of the steps of the process of FIG. 10.

The components of unit 146 are illustrated in FIG. 11. The components of FIG. 11 incorporate units 152-170, which correspond with units 90-110 of FIG. 8. The units of FIG. 11 calculate "part 3" of the tertiary coincidence, while the corresponding units of FIG. 8 calculate "part 3" of the binary coincidence.

Figure 12:
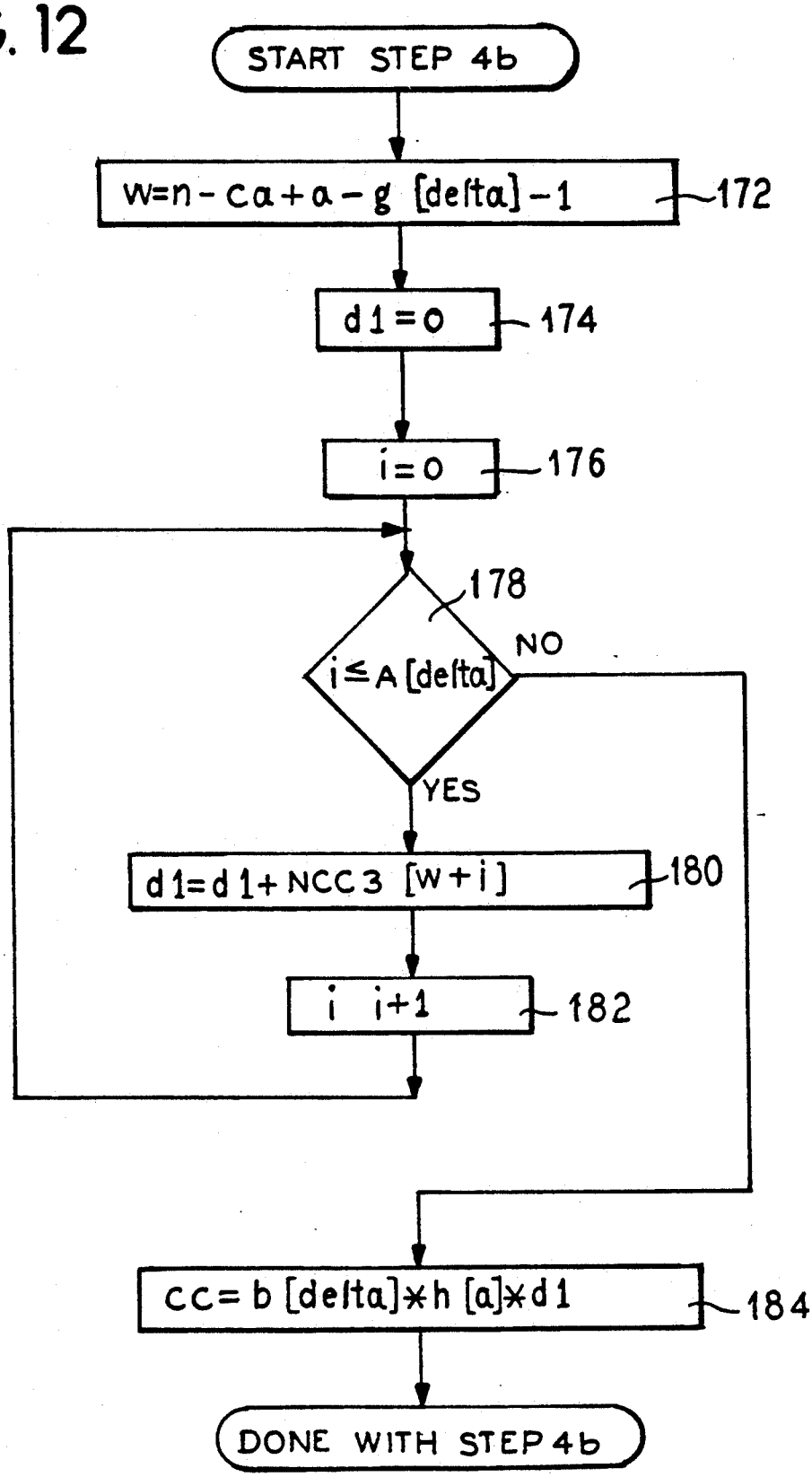
FIG. 12 is a flowchart of one of the steps of the process of FIG. 11.

The components of unit 164 are illustrated in FIG. 12. Units 172-184 of FIG. 4 correspond to units 112-124 of FIG. 9, except that the units of FIG. 12 calculates CC for the tertiary coincidence, while the corresponding units of FIG. 9 make the calculation for the binary coincidence.

Figure 13:
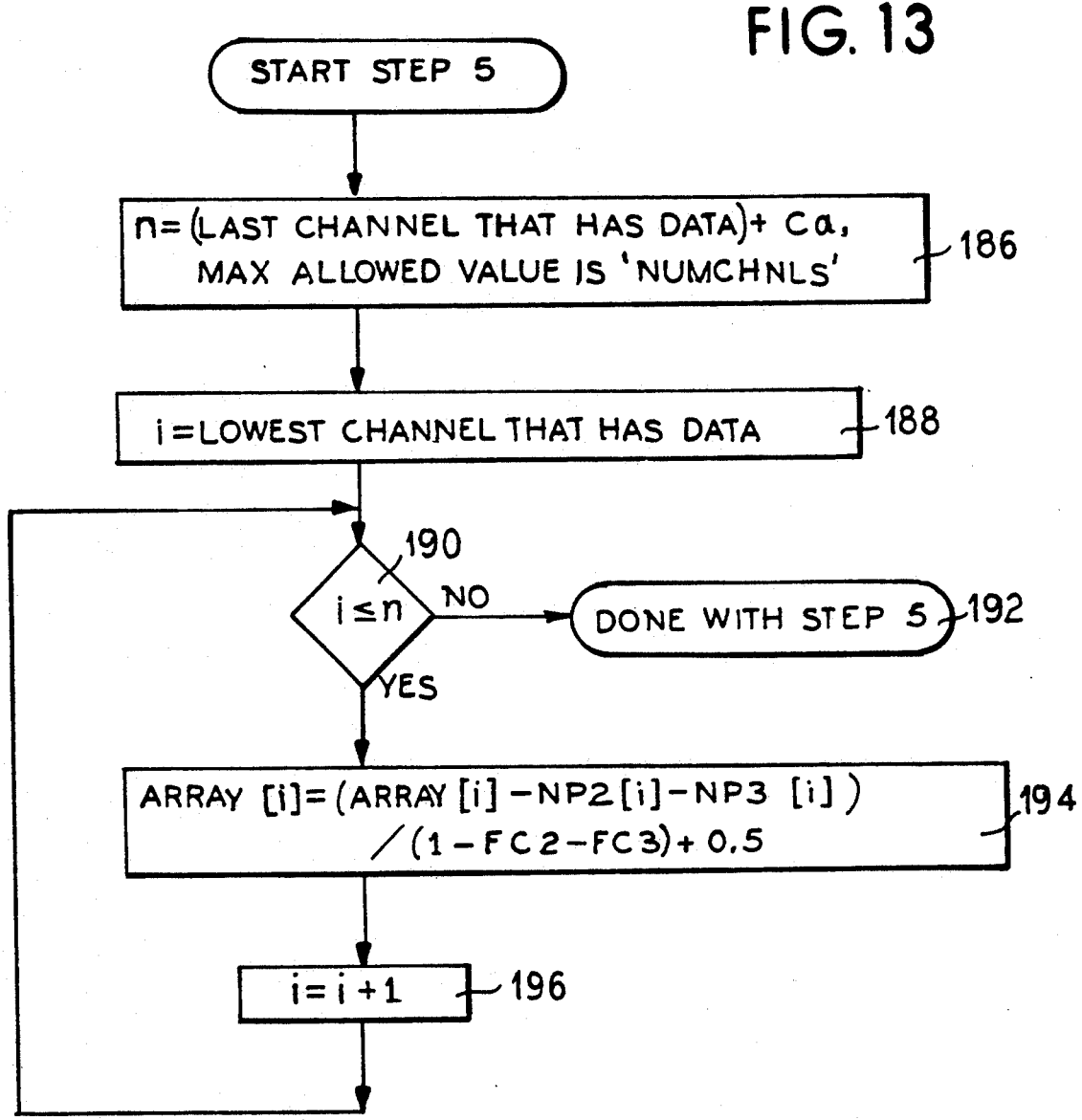
FIG. 13 is a flowchart of the process of step 5 of FIG. 4.

When path 132 (FIG. 10) receives control from unit 130, control passes to unit 28 of FIG. 4. FIG. 13 illustrates the components of unit 28. Control passes first to unit 186, which again calculates the value n which is the same as the value calculated in units 62 and 128. Then the index i is set by unit 188 to the lowest channel that has data, and control passes to unit 190. If i is not less than n, control passes to an exit over path 192, and the correction process is complete. Otherwise, control passes to unit 194, which adjusts the element i of the array A in accordance with the binary coincidence correction stored in element i of array NP2, and the tertiary coincidence correction stored in element i of array NP3. Then unit 196 increments i and returns control to unit 190. The loop including units 190-196 is repeated until all of the elements of the array which contain data have been adjusted to account for the binary and tertiary coincidence correction.

It is apparent that the present invention affords a simple and effective means of modifying particle count data to correct for coincidences. The entire operation is performed rapidly, and results in data which represents an precise particle distribution histogram of the sample under investigation, irrespective of its concentration, i.e., independent of the number of coincidences actually experienced within the sensing zone. The use of the present invention makes it unnecessary to modify samples to reduce the proportion of coincidences, since the presence of coincidence does not result in inaccurate data.

The present invention also makes it possible to perform the coincidence corrections sufficiently rapidly so that dynamic conditions may be investigated in real time.

It will be apparent that various modifications and additions may be made in the apparatus and methods of the present invention, without departing from the essential features of novelty thereof, Which are intended to be defined and secured by the following claims.

What is claimed:

1. A method of measuring particle distribution within a suspension of particles in liquid, comprising the steps of passing the suspension through the sensing zone of apparatus for sensing discrete particles, deriving from said sensing apparatus a plurality of values corresponding to a first approximation of the number of particles in each of a plurality of different sizes, calculating a coincidence correction factor for each of said values, and correcting each of said values individually by applying its respective coincidence factor, said coincidence correction factor being derived from said first approximation data for a range of said values to compensate for the fact that a number of particles represented by each of a plurality of such values is partially due to coincidence of multiple particles having smaller sizes which are coincident when passing through said sensing zone, whereby said measuring may be accomplished without requiring dilution of the sample to an extent which renders coincidence practically negligible.

2. The method according to claim 1, including the step of calculating a correction for one of said values, said correction being based on said first approximation data for said one value and the first approximation data for other values representing the coincidence of particles of said one value with another particle.

3. The method according to claim 1, including the step of calculating a correction for one of said values, said correction being based on the first approximation data for said one value, and the first approximation data for other values representing particles of smaller sizes which coincide in said sensing zone to produce said first approximation data assigned to said one value.

4. The method according to claim 1, including the step of calculating a correction, said correction being determined partially by the number of particles participating in coincidences.

5. The method according to claim 4, including the step of deriving the number of particles participating in coincidences from the number of particles contained in a volume of fluid scanned during the sensing time of said electrozone apparatus.

6. The method according to claim 5, including the step of determining the number of particles participating in coincidence as determined from the number of particles resident in the sensing volume during the sensing time, plus the number of particles resident in a fluid space which enters said sensing volume during a time interval following said measuring time.

* * * * *